(12) United States Patent
Bunnelle

(10) Patent No.: US 8,048,054 B2
(45) Date of Patent: Nov. 1, 2011

(54) DISPOSABLE ARTICLE TAB ATTACHMENT ADHESIVE

(75) Inventor: William L. Bunnelle, Ham Lake, MN (US)

(73) Assignee: Adherent Laboratories, Inc., St. Paul, MN (US)

( * ) Notice: Subject to any disclaimer, the term of this patent is extended or adjusted under 35 U.S.C. 154(b) by 954 days.

(21) Appl. No.: 11/582,842

(22) Filed: Oct. 17, 2006

(65) Prior Publication Data

US 2007/0083183 A1  Apr. 12, 2007

Related U.S. Application Data

(63) Continuation-in-part of application No. 10/970,092, filed on Oct. 21, 2004, now abandoned.

(51) Int. Cl.
*A61F 13/15* (2006.01)
*A61F 13/20* (2006.01)

(52) U.S. Cl. ............... 604/389; 604/386; 24/304

(58) Field of Classification Search ........... 604/386–391
See application file for complete search history.

(56) References Cited

U.S. PATENT DOCUMENTS

| | | | |
|---|---|---|---|
| 5,019,071 A * | 5/1991 | Bany et al. ............ | 604/389 |
| 5,019,073 A | 5/1991 | Roessler et al. | |
| 5,066,289 A | 11/1991 | Polski | |
| 5,071,415 A | 12/1991 | Takemoto | |
| 5,176,671 A | 1/1993 | Roessler et al. | |
| 5,302,675 A | 4/1994 | Sustic et al. | |
| 5,429,630 A * | 7/1995 | Beal et al. ............ | 604/385.04 |
| 5,459,184 A | 10/1995 | Bunnelle et al. | |
| 5,624,986 A | 4/1997 | Bunnelle et al. | |
| 5,627,229 A | 5/1997 | Bunnelle et al. | |
| 5,637,665 A | 6/1997 | Sustic et al. | |
| 5,681,913 A | 10/1997 | Sustic et al. | |
| 5,714,554 A * | 2/1998 | Sustic et al. ............ | 526/125.3 |
| 5,723,546 A | 3/1998 | Sustic | |
| 6,017,621 A | 1/2000 | Hilston et al. | |
| 6,080,818 A | 6/2000 | Thakker et al. | |
| 6,180,708 B1 | 1/2001 | Chu | |
| 6,195,850 B1 | 3/2001 | Melbye et al. | |
| 6,277,479 B1 | 8/2001 | Campbell et al. | |
| 6,319,979 B1 | 11/2001 | Dubois et al. | |
| 6,384,297 B1 | 5/2002 | Colman et al. | |
| 6,393,673 B1 | 5/2002 | Kourtidis et al. | |
| 6,419,667 B1 | 7/2002 | Avalon et al. | |
| 6,531,207 B1 | 3/2003 | Eaton et al. | |
| 6,541,679 B2 | 4/2003 | Betrabet et al. | |
| 6,550,633 B2 | 4/2003 | Huang et al. | |
| 6,582,762 B2 | 6/2003 | Faissat et al. | |
| 6,612,462 B2 | 9/2003 | Sosalla et al. | |

(Continued)

OTHER PUBLICATIONS

"Huntsman RT 2730," Huntsman Corporation, 1 page (Jul. 1999).

(Continued)

*Primary Examiner* — Melanie J Hand

(74) *Attorney, Agent, or Firm* — Pauly, DeVries Smith & Deffner, L.L.C.

(57) ABSTRACT

The invention relates to a disposable article and method relating to attachment tabs on a disposable article. The disposable article typically comprises a non-woven layer, an absorbent layer, and an outer film-wrapping layer associated with an attachment tab. The tabs are adhered to the polymer film and can be used to close the absorbent garment when in use. The invention also relates to a method of attaching the tabs to the polymer film using an adhesive having improved adhesive properties.

66 Claims, 2 Drawing Sheets

U.S. PATENT DOCUMENTS

| | | |
|---|---|---|
| 6,719,744 B2 | 4/2004 | Kinnear et al. |
| 7,045,028 B2 | 5/2006 | Betrabet et al. |
| 2003/0153894 A1 | 8/2003 | Gibbs et al. |
| 2004/0236300 A1 | 11/2004 | Gibbs et al. |
| 2004/0238095 A1 | 12/2004 | Johnson |
| 2006/0089617 A1 | 4/2006 | Bunnelle |

OTHER PUBLICATIONS

"Huntsman RT 2830," Huntsman Corporation, 1 page (Sep. 2004).
"Huntsman RT 2880," Huntsman Corporation, 1 page (Jul. 1999).
"Huntsman REXtac® APAO Polymers," Huntsman Corporation, 14 pages (Copyright 1999).
"Vector 4211A Styrene-Isoprene-Styrene (SIS) Block Copolymer," Dexco Polymers LP, 2 pages (Jul. 2005).
Temin, "Pressure Sensitive Adhesives for Tapes and Labels", *Handbook of Adhesives*, Third Edition, Ch. 38, p. 641 (1990).
ASTM International Designation: D 6463/D 6463M-06, "Standard Test Method for Time to Failure of Pressure Sensitive Articles Under Sustained Shear Loading", pp. 1-4 (Jul. 27, 2009).

* cited by examiner

DISPOSABLE ARTICLE TAB ATTACHMENT ADHESIVE

RELATED APPLICATION

This application is a continuation-in-part application of U.S. Ser. No. 10/970,092 filed Oct. 21, 2004 now abandoned which is expressly incorporated by reference herein.

FIELD OF THE INVENTION

The invention relates to an adhesive or mechanical closure tab used on a disposable article using adhesive or mechanical fastening means. The tab has an attachment adhesive used to fix or hold the tab on the article. The tab also has a positioning means such as a mechanical system or an adhesive to close and position the article on the user. Such articles typically comprise a diaper, an adult incontinent pads or similar structures. The adhesive closure or tab requires a layer of an attachment hot melt adhesive that provide a unique set of attachment properties compared with prior adhesive materials. The invention relates to a tab structure, a disposable article and a method of use. The attachment adhesive secures the tab to the article at high temperature for an extended period.

BACKGROUND OF THE INVENTION

The invention relates to a tab or closure system adhered to an outer film or non-woven wrapper in a disposable absorbent article. The tab or closure is adhered to the film wrapper or outer non-woven cover of the article with an attachment adhesive. In particular, the invention relates to a unique attachment adhesive having enhanced properties for attaching the tab to the film or non-woven. The tab closure system comprises a flexible film having, on one end, means to substantially permanently attach the tab to the disposable article and, on the opposite end, a positioning means such as a mechanical attachment system or a layer of adhesive that can hold the tab to the polymer film outer wrapper or outer non-woven layer during application, positioning, closure or repositioning.

Disposable absorbent articles typically include disposable diapers, adult incontinent pads and other systems for retaining or absorbing substantial quantities of bodily fluids. Such articles are typically used by placing or positioning the disposable article on a human subject and then closing and positioning the article on the subject with closure tabs securing the article to the subject. The tabs are attached to the article during manufacture with an attachment adhesive. The closure tabs also have a mechanical fastening system or a layer of a pressure sensitive adhesive (PSA) that positions or holds the tab to the outer polymer film layer or outer non-woven layer, and act to position or reposition the disposable article. Tabs are generally placed at corner positions of one end of the article and are adhered to opposite ends of the article. Typical fastening tabs have one end which is substantially permanently attached and bonded to the absorbent article and a second free end, which can be attached to the opposite end and used to position or reposition, or maintain the article in place on the user. Typically, the tab is initially attached or bonded to the polymer layer or non-woven with a substantially permanent adhesive during manufacture. In the instance that the positioning adhesive comprises a hot-melt pressure sensitive system, the adhesive used to close or position the article can be the same adhesive than is used to attach the tabs to the corner of the disposable article. When different formulations are used for attachment and positioning, the tab attachment adhesives are typically formulated to permanently attach the tabs to the polyolefin film while the positioning or closure adhesives can be less aggressive and can sometimes be a repositionable hot-melt pressure sensitive adhesive (HMPSA).

One example of a typical tab attachment adhesive is shown in Bany et al., U.S. Pat. No. 5,019,071. That adhesive comprises a styrene/isoprene AB or ABA block copolymer, a solid $C_5$ tackifying resin combined with a diluent aromatic containing aliphatic plasticizing oil. The adhesive disclosed by Bany et al. includes about 33-50 wt % of block copolymer, a plasticizing oil comprising 5 to 45% aromatic, the balance being aliphatic, and a solid essentially aliphatic tackifying resin. This adhesive and the adhesive HL-1696 sold by HB Fuller Company, comprising an SIS triblock polymer, a Benzoflex plasticizer and a tackifier, are characteristic of the tab attachment adhesives currently on the market in this general market.

The tab attachment adhesive of the invention is a substantially permanent adhesive, is typically non-pressure sensitive and has a substantial static shear character. These adhesives are a substantially different class of adhesives than the typical pressure sensitive adhesive used in positioning or adhering absorbent articles to undergarments. One example of such a pressure sensitive adhesive is shown in Beal et al., U.S. Pat. No. 5,429,630. The absorbent article has an elongated shape having an absorbent surface tabs 26 and 28. The Beal et al. article is shown in FIGS. 1 and 2. The absorbent article and the tabs have a pressure sensitive adhesive used to adhere the article to the undergarment. Such a structure does not contain a tab that is attached to an absorbent article using a non-pressure sensitive, substantially permanent adhesive having high shear. In Beal et al., the tabs are adhered not to the absorbent article, but to the undergarment for positioning purposes using a different class of adhesive.

In the past, the attachment adhesives have been difficult to use. In large part, the adhesives used to attach the tabs to the polymer (e.g.) polyolefin film tend to have a relatively short open time, i.e., the time during which the adhesive can form substantially permanent bonds to the polymer film. Such short open times limited manufacturing flexibility. Once the adhesive bonds were formed, the bonds often failed to have either sufficient tensile strength or failed to maintain such bonds at temperatures (i.e. body temperatures) in shear conditions in excess of 100° F. Adhesives that do not meet these criteria often fail to attach the tabs permanently to the polymer film for successful manufacturing purposes.

Substantial need exists for an attachment adhesive for use with a tab and a polymer film having a substantial open time, tensile strength and the ability to survive with a permanent attachment for a substantial period of time at or above 100° F.

BRIEF DISCLOSURE OF THE INVENTION

The invention relates to an adhesive tab in a disposable article. Such a tab comprises a polymer film with positioning means and an attachment adhesive. The positioning means can comprise, on one end, a mechanical or adhesive positioning system. Such an adhesive closure tab is substantially permanently attached to one end of the article with the attachment adhesive of the invention. The attachment adhesive comprises sufficient open time, tensile strength and shear strength to maintain the tab in place under typical manufacturing, transportation, storage and use conditions. The positioning adhesive comprises a layer of PSA that can be used to position and adhere the tab to an opposite end of the article. The PSA positioning adhesive is often covered by a release liner protecting the adhesive from loss of adhesive properties or contamination during manufacturing, storage, packaging or sale. The positioning means also includes a mechanical system can comprise a hook and loop, button, snap, Velcro or other mechanical system.

We have found a unique tab structure for disposable article construction. The tab typically comprises, on a first end, an attachment adhesive that substantially permanently attaches one tab end to the absorbent article exterior or film. The other end of the tab comprises a mechanical closure or adhesive closure used to hold the article closed and positioned on the subject individual. A hot melt PSA layer can be used to position the tab to the absorbent article opposite end for positioning or repositioning purposes. The adhesive layers are coated into the polymer film tab. The improved attachment adhesive of this application provides enhanced open time, bond strength and temperature stability.

For the purpose of this disclosure, the term "adjacent end" refers to the end of the disposable article to which the tab is substantially permanently attached. The term "opposite end" refers to the end of the disposable article to which the tab is adhered during positioning of the disposable article. The term "mechanical positioning means" and "positioning adhesive" relate to mechanical or adhesive means used to close and position the absorbent article when placed on a user. The "mechanical positioning means" can be, e.g., a Velcro attachment or a snap closure. The "positioning adhesive" is a layer on the tab that attaches the tab to the film or non-woven for positioning purposes. The term "attachment adhesive" relates to an adhesive than is used to substantially permanently adhere the tab to the adjacent end of the article to a polymer film or non-woven during initial manufacture of the absorbent article and to maintain the tab on the absorbent article during manufacture, packaging, storage and use. For the purpose of this disclosure, the term "poly-alpha olefin" means a poly-alpha olefin that has less than 10% crystallinity. The preferred poly-alpha olefin material is a high 1-butene atactic polyalphaolefin. The term "high butene polyalpholefin" typically indicates that greater than 50 wt % of the polymer comprises a 1-butene monomer. Often the 1-butene monomer is present in an amount greater than about 60 wt %, often greater than about 75 wt % of the polymer typically polymer comprises 60 to 70% 1-butene with 30 to 40% propylene and minor amounts of other monomers. Other monomers that can be present in the polyalphaolefin material include, typically, ethylene, propylene, 2-butene, isobutene, and other higher olefin and monomer materials.

We have found that a permanent tab attachment adhesive can be made using an effective amount of an amorphous polyalphaolefin polymer comprising a 1-butene monomer. The preferred polymer has a tensile strength of about 50 to 600 psi, 75 to 450 psi or about 300 to 4000 kPa, 500 to 3100 kPa (ASTM E28) and Brookfield viscosity that is greater than about 2500 cP, 2700 cP or 4000 cP at 190° C. measured with spindle #27 at 5 RPM on a Brookfield viscometer (ASTM D3236). The adhesive comprises a needle penetration of about 0.5 to 2 mm (5 to 20 dmm) (ASTM D1321), a Ring and Ball softening point of less than 100° C. (ASTM D638), a glass transition temperature ($T_g$) less than about 30° C. (ASTM D3417) and an open time greater than about 150 or 200 seconds, often greater than 400 seconds.

We have found that these polyalphaolefin polymers primarily based on 1-butene monomers satisfy these demanding characteristics. Surprisingly, the polymer itself, in the absence of tackifying agents, plasticizer materials, extending agents, or any other adhesive components, can adequately provide tab attachment and survive the rigorous parameters discussed above. The following polymers from Huntsman meet the requirements.

TABLE 1

Useful Polymers

| Polymer | 1-Butene | Propylene | Tensile str. kPa | R&B ° C. | Visc. (cP) | Open Time (sec) | Needle Penet. (mm) | Tg ° C. |
|---|---|---|---|---|---|---|---|---|
| RT-2830 | 60-70% | 30-40% | 1230 | 90 | 3000 | >240 | 2.5 | −23 |
| RT-2880 | 60-70% | 30-40% | 3000 | 93 | 8000 | >240 | 8 | −35 |

These polymer materials are disclosed in Sustic et al., U.S. Pat. Nos. 5,302,675 and 5,637,665.

DETAILED DISCUSSION OF THE INVENTION

Figure 1:
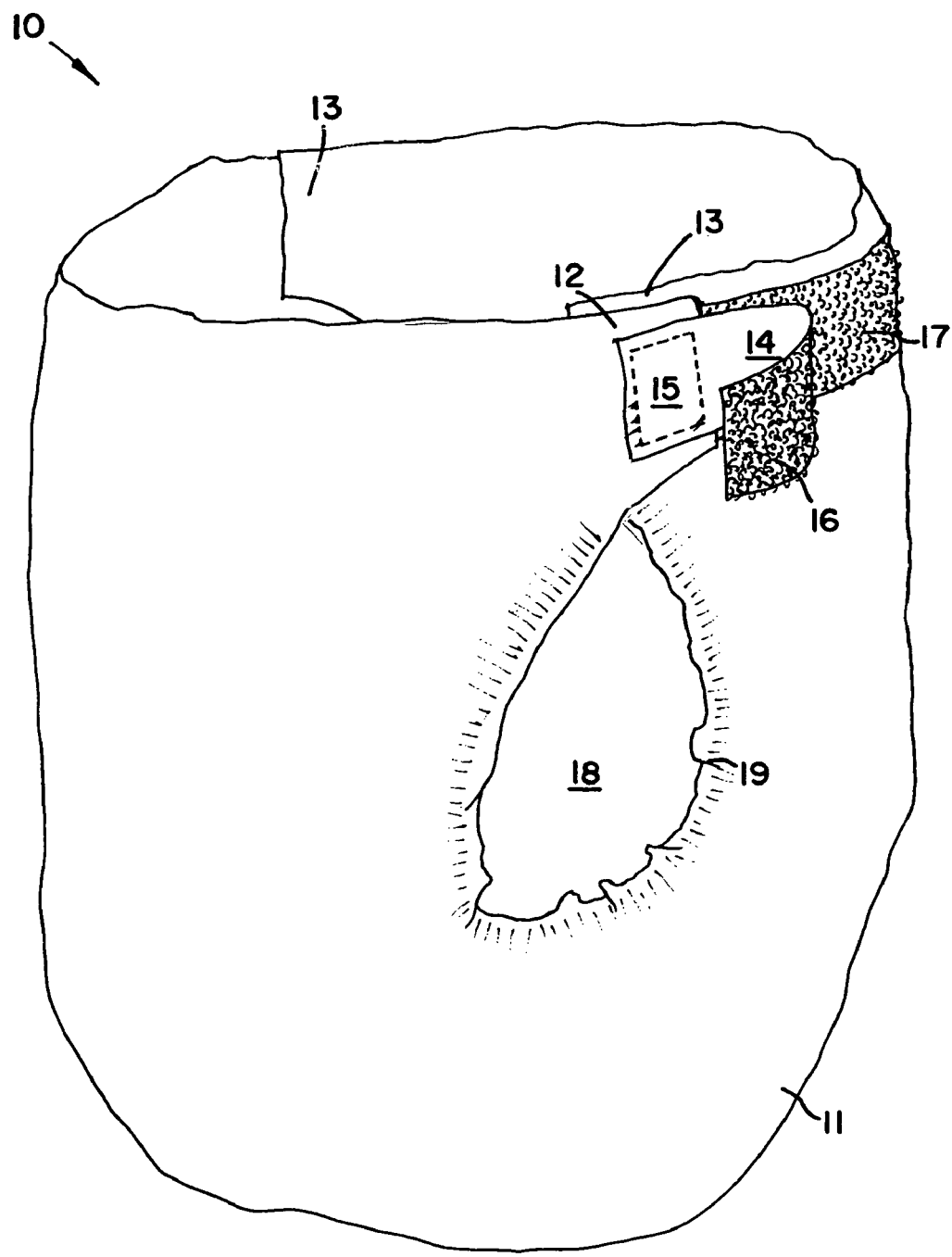
FIG. 1 shows one aspect of the invention in a typical diaper embodiment.

One aspect of the invention is a flexible attachment tab on a disposable article. A second aspect of the invention is a disposable article having one or more attachment tab structures in the disposable article structure. An important component of the tab is adhesive used to attach the tab to an adjacent end of the disposable article. A final aspect of the invention is a method of making a disposable article by adhering the tab to a film layer with the adhesive.

Disposable Article Construction

A disposable article typically comprises a thin flexible often-stretchable exterior layer. This layer can contain the outer abundant portion of the article. The outer layer is often a non-woven layer, a polymer sheet or film. Within the outer layer is typically placed on absorbent layer or absorbent core structure. Over the absorbent layer is typically placed a non-woven sheet separating the user from the absorbent layer. Such absorbent article is typically shaped to the user and often contains attachment tabs to hold the article in place after positioning. The absorbent article can comprise a variety of other elements. Such an article can comprise for example, a belt attachment, a moisture indicator system, multiple absorbent layers, elastic leg closures, moisture barriers at a leg opening or waist opening and other features well known in the absorbent article construction.

Tab System

Tabs are used to close and position the article. Opposite edges, typically opposing ends, of the article are brought close to another, in substantial contact with one another or in an overlapping position. Once located in such a position, tabs fixed to one surface are adhered to an adjacent surface with a pressure sensitive adhesive to hold the article in place after positioning. Tabs are typically fixed to one surface with permanent adhesives while the opposite end of the tab is coated with an adhesive formulated and configured for a positioning role. Once the tabs are fixed in place, the article defines by openings and a surrounding waist branch. The invention is used to place a diaper tab attachment onto the polymer film or non-woven outer layer of the absorbent article construction. Tabs are small portions of film with an attachment adhesive and a positioning system. The tabs are 0.1 to 0.5 mm in thickness, about 5 to 15 cm in length and 1 to 5 cm in width. The tabs can have extra portions to wrap the article for mechanical integrity.

The tab can be a typical adhesive tab or can include a mechanical fastener. The variety of mechanical fasteners can be used including snaps, hooks and others. One preferred mode involves the use of a hook and loop mechanical fastener system, also known as a Velcro type structure. Velcro fasteners have been specifically developed for use in disposable articles such as diapers and incontinent pads. Hook and loop materials are appropriately sized, light in weight and provide a secure attachment capable of removal and replacement for multiple openings and closings for a variety of reasons. The Velcro fastener is light in weight, soft, flexible, cost sensitive, but obtains excellent fastening and can be used for the smallest of infants and the largest adult requiring incontinent protection.

In use, the polymeric amorphous polyalphaolefin material is layered onto either the polymer film or the tab material and then brought into intimate contact to form an attachment adhesive joint between the polymer film and the tab attachment. The joint to permanently adheres the tab to the film. The polymer is applied in the form of a film having a thickness of about 0.02 to 0.2 mm or about 0.05 to 0.1 mm (about 2 to 8 mil) and an add on amount of about 1 to 10 or about 2 to 4 $g\text{-}m^{-2}$. The adhesive material is typically applied in thin layers using conventional film forming equipment in melt form at a temperature that exceeds about 150° C., typically about 150 to 175° C. Such equipment includes a slot die application nozzle(s) commercially available from Nordson corporation, ITW, May Coating and others.

Velcro type fasteners have a first mechanical portion called the hook and a second mechanical portion called a loop structure. The hook structure has multiple hooks on an attachment structure, while the loop has multiple loops on the loop structure. Hooks typically comprise a high modulus polyolefin. The hook can engage the loop and maintain the connection for a desired useful lifetime. The high modulus polymer defines the strength of the hold. The high modulus of the hook ensures that the hook will stay engaged with the loop under substantial stress, but when placed under sufficient stress to remove the fastener, the fasteners can be readily removed for a purpose. Modulus up to 150,000 psi is often useful to obtain the appropriate stiffness.

The loop structure typically comprises a fabric having a large number of raised loops in an orientation such that they can be readily engaged or snagged by the hook system. The typical loop system is a woven fabric having raised loops. The hook system and the loop system, once engaged, provides about 5 to 25 pounds per square inch substantial peel strength of about 250 to about 1500 grams per lineal inch.

The tab fastener structures of the invention are typically installed onto a plastic sheet acting as the outside layer of the absorbent article. Such sheets are liquid safe polymer films with minimum elasticity. Examples include polyethylene film, polypropylene film, polyester film, plasticized polyvinyl chloride and other flexible, thin, low cost films. For purposes of obtaining flexibility and ease of manufacture, the film typically ranges from about 0.5 to about 0.0002 of an inch in thickness. The exterior sheet is typically liquid safe, but provides substantial permeability for breathability purposes.

The films can be microporous. The absorbent article typically comprises an absorbent that, held within the back sheet, often contains a non-woven inner liner. The interior inner liner comprises a highly permeable material such as a spun bonded, non-woven structure that readily passes moisture from the interior of the diaper into the absorbent bat. The absorbent bat or structure formed within the absorbent article typically comprises a pad, commonly of cellulosic or wood pulp fluff for the purpose of substantially absorbing liquid materials released within the absorbent article. The bat can comprise a mixture of cellulosic fiber and synthetic fiber such as blends of wood fluff and polyethylene or polypropylene fibers having substantially indeterminate length, but fiber diameters of about 0.05 to about 25 microns. The absorbent bat can also include highly absorbent materials to increase the absorptive capacity of the absorbent article. These materials can be organic, however, they tend to be highly absorbent organic polymer materials. Organic materials that can be used as highly absorbent materials include natural gums and resins, but preferably include synthetic polymeric material such as hydrogels including carboxy methyl cellulose, alkali metal salts of acrylic polymers, polyacrylimides, poly(vinyl-alcohol), poly(ethylene-maleic anhydride) polymers and copolymers, poly(vinyl-ethers) polymers and copolymers, hydroxyalkyl cellulose, poly(vinyl sulfonic acid) polymers and copolymers, poly(acrylic) polymers, poly(vinylpyrrolidone) and polymer vinyl pyrrolidone, and others. Additionally, a variety of functionalized starches can also be used. The absorbent article can also contain a variety of other ingredients that cooperate with the fluid proof external film, the internal non-woven layer or the absorbent bat formed therebetween. Such useful elements include a tissue wrap around the absorbent article to maintain the mechanical stability of the absorbent bat, the absorbent article can contain elastic waist bands and leg bands and can contain an exterior stretchy layer or an exterior woven or non-woven fabric layer.

Non-woven Exterior Layer

A non-woven fabric is typically considered a generally planar structure produced by loosely bonding together yarns or rovings of natural or synthetic fibers. Non-woven materials are typically manufactured by randomly placing fibers or rovings in a substantially random pattern without the benefits of a woven structure. The random fibers are then generally thermally bonded using either the inherent bonding characteristics of the multiple fibers or by bonding the fibers together with a thermally activated adhesive material. The non-woven layers are typically moderately stretchy but breathable or permeable layers. Various polymers can be used to make the non-woven materials including polyolefins, polyesters, ethylene vinylacetate polymers, ethylene acrylic polymers and others.

Microporous Breathable Films

A breathable microporous film can also be used in the structure of the invention. Such films typically are stretched filled-film comprising a thermal plastic polymer and typically organic or inorganic filler material. In manufacturing such layers, the components are mixed, heated and extruded into a monolayer or multi-layer sheet. A variety of film forming processes can be used to make the sheet including casting or blowing processes and equipment. Such film can be stretched in one, two or more directions to change the polymer orientation reduced film gauge or alter the microporous structure (size and/or frequency) of the film. Virtually any known thermal plastic or blend there of can be used to make the breathable microporous films including polyethylenes, polyolefins, polyesters, ethylene vinylacetate polymers, ethylene acrylic polymers, polyamides including nylon polymers, polystyrenes, polyurethane, polybutane, etc.

Polymer Film

A variety of polymer sheet-like materials can be used as the exterior layer liquid impervious film. In one aspect of the invention, a non-woven material can provide a more cloth like exterior appearance that can cover the polymer film on the exterior of disposable article. The exterior layer can comprise a single layer of the polymer film or can comprise a multilayer structure. Such structures can comprise a variety of materials in each layer and the layers can be adhered one to the other for structural integrity. Typical polymer sheet materials often comprise the largest having high tensile strength another high strength characteristics. Thermoplastic polymers are preferred and include such materials such as polyester materials, polyolefin materials another thermoplastic that can be made into thin sheet-like feedstock. Examples of polyester polymers include polyethylene terephthalate and polybutylene terephthalate materials. Other aromatic diacids and polyols can be used in the manufacture of such polymers. Examples of useful polyolefin materials include polyethylene, polypropylene, ethylene/propylene copolymers, ethylene/propylene/diene polymers and others. Often the polymer materials are formed into sheets and treated to improve strength flexibility and puncture resistance. Often the films are biaxially oriented, heat treated or surface treated. Such a service treated materials may obtain a matter finish, glossy finish, powdered finish, embossed or printed surface. Such polymer film often have a thickness that ranges up to 80 micrometers often about 10 to 50 micrometers.

Absorbent Layer

An absorbent layer, pad or batt is included in the absorbent article. The absorbent layer can be made from any suitable fibrous absorbent material. Such fibrous material can be combined with other absorbent fibers, particulate materials or other highly absorbent or fluid absorbing structures. Preferred absorbent fibers include cellulosic fibers manufacture from wood pulp commonly known as "fluff."

Non-woven Interior Layer

In the disposable article, the absorbent layer is positioned between the exterior film and an interior non-woven liquid permeable layer. The inner liquid permeable layer or non-woven liner often is manufactured from a soft, flexible, fluid pervious non-woven through which fluid readily passes into the absorbent layer. The non-woven liner increases the comfort of the user. The non-woven one or typically comprises a non-woven web or perforated sheet made from polyolefin materials. Such nonevents include paper tissue layers having substantial what strength, non-woven filament sheets made of polyolefin fibers perforated polyolefin combs and similar structures. The liner can be mechanically fixed to the edges of the polyolefin exterior sheet and can often be attached to the absorbent layer as well.

DETAILED DISCUSSION OF DRAWINGS

FIG. 1 shows a tab closure system using the hook and loop closure also known as Velcro® system. The absorbent article or diaper 10 of FIG. 1 is made with a general over wrap 11 which is typically a non-woven or polymer film outer wrap. The outer wrap covers an absorbent bed or mat (not shown) held within the article. The closure system is typically mounted on the outer wrap 11. The closure system typically comprises a tab 14 containing an array of hooks 16 that adheres to a structure comprising a loop system 17. The tab 14 is adhered to the outer wrap 11 using adhesive 15 shown in phantom. The loop system is adhered to the outer wrap 11 using conventional adhesives or the adhesive of the invention. The tab portion 14 is adhered to the outer wrap 11 using adhesive 15 and 12 of the disposable article. The loop system 17 is placed on an opposite end of the absorbent article 13. The absorbent article 10 can contain a variety of other useful structures and absorbent article instruction including, for example, a leg elastic 19 bonded to the outer wrap 11 forming a leg opening 18.

FIG. 1 shows a tab closure system using the hook and loop closure also known as Velcro® system. The absorbent article or diaper 10 of FIG. 1 is made with a general over wrap 11 that is typically a non-woven or polymer film outer wrap. The outer wrap covers an absorbent bed or mat (not shown) held within the article. The closure system is typically attached to the outer wrap 11. The closure system typically comprises a tab 14 containing an array of hooks 16 that adheres to a structure comprising a loop system 17. The tab 14 is attached to the outer wrap 11 using adhesive 15 shown in phantom. The loop system is adhered to the outer wrap 11 using conventional adhesives or the adhesive of the invention. The tab portion 14 is adhered to the outer wrap 11 using adhesive 15 to layer 12 of the disposable article. The loop system 17 is placed on an opposite end of the absorbent article 13. The absorbent article 10 can contain a variety of other useful structures and absorbent article instruction including, for example, a leg elastic 19 bonded to the outer wrap 11 forming a leg opening 18.

Figure 2:
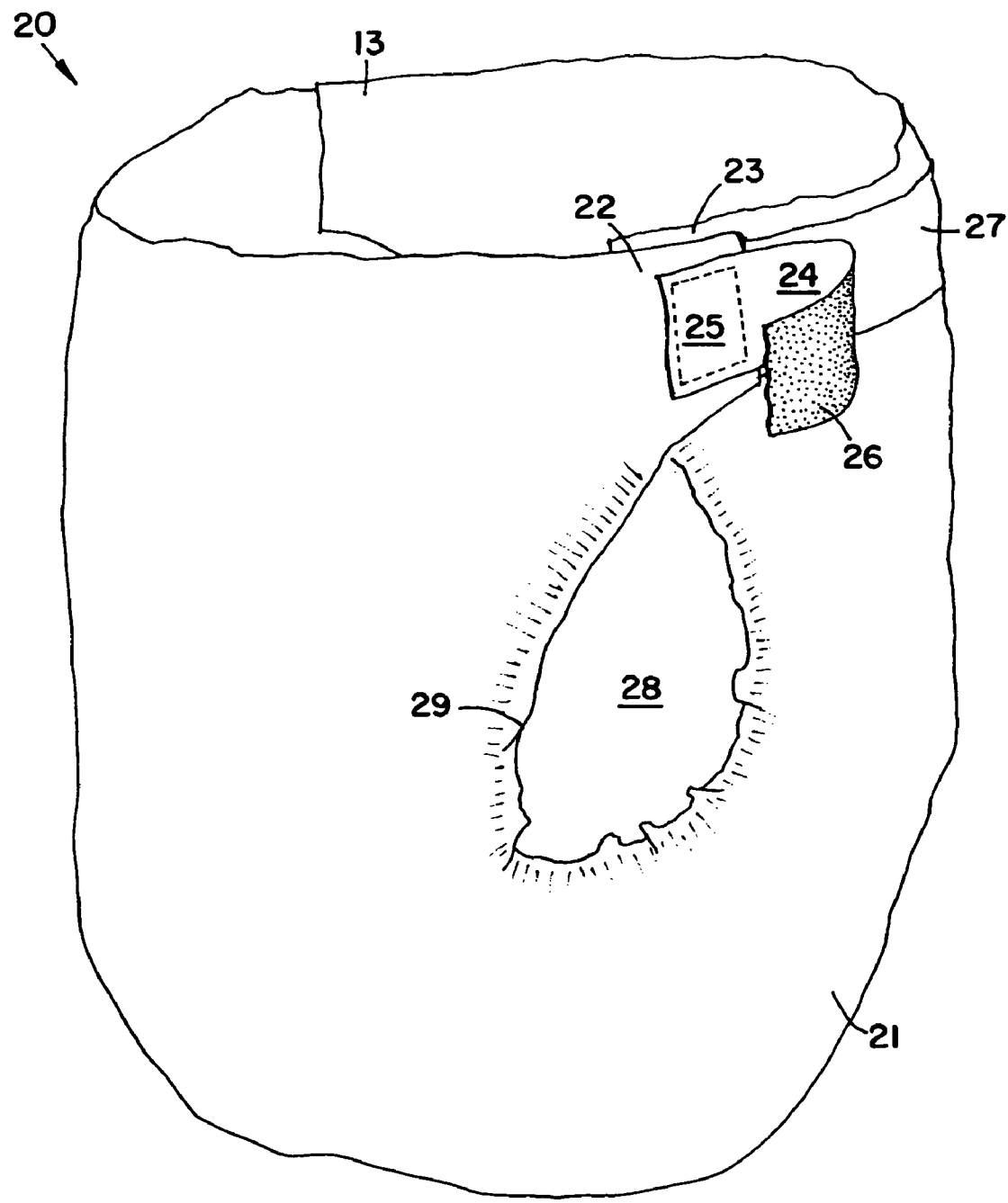
FIG. 2 shows a second aspect of the invention in a typical diaper embodiment.

FIG. 2 shows an alternate tab closure system using the hook and loop closure also known as Velcro® system. The absorbent article or diaper 20 of FIG. 2 is made with a general over wrap 21 that is typically a non-woven or polymer film outer wrap. The outer wrap covers an absorbent bed or mat (not shown) held within the article. The closure system is typically attached to the outer wrap 21. The closure system typically comprises a tab 24 containing an adhesive 26 that positions the tab to an attachment surface 27. The tab 24 is attached (adhered) to the outer wrap 21 using adhesive 25 shown in phantom. The tab 24 is positioned on an opposite end of the absorbent article 20. The absorbent article 20 can contain a variety of other useful structures and absorbent article instruction including, for example, a leg elastic 29 bonded to the outer wrap 21 forming a leg opening 28.

Experimental

TABLE 2

Static Shear Strength Testing

| Product @ 2 mil, 3 mil and 4 mil | Pass/Fail | TRIAL | | | | | |
|---|---|---|---|---|---|---|---|
| | | 1 (min) | 2 (min) | 3 (min) | 4 (min) | 5 (min) | 6 (min) |
| Comparison 1 | Fail | 12 | 8 | 44 | 13 | 26 | 33 |
| Comparison 1 | Fail | 68 | 84 | 103 | 84 | 92 | 69 |
| Comparison 1 | Fail | 160 | 110 | 142 | 184 | 180 | 93 |
| Comparison 2 | Fail | 16 | 13 | 22 | 24 | 9 | 27 |

TABLE 2-continued

Static Shear Strength Testing
TRIAL

| Product @ 2 mil, 3 mil and 4 mil | Pass/Fail | 1 (min) | 2 (min) | 3 (min) | 4 (min) | 5 (min) | 6 (min) |
|---|---|---|---|---|---|---|---|
| Comparison 2 | Fail | 29 | 54 | 37 | 63 | 46 | 60 |
| Comparison 2 | Fail | 68 | 110 | 126 | 113 | 89 | 167 |
| Comparison 3 | Fail | 670 | 653 | 890 | 641 | 554 | 598 |
| Comparison 3 | Pass | 1121 | 986 | 1320 | 989 | 841 | 1153 |
| Comparison 3 | Pass | 1240 | 1168 | DNF | DNF | 1296 | 1341 |
| RT-2830 (estimate @ 2 mil) | Pass | DNF | | | | | |
| RT-2880 | Pass | DNF | DNF | DNF | DNF | DNF | DNF |
| RT-2880 | Pass | DNF | DNF | DNF | DNF | DNF | DNF |
| RT-2880 | Pass | DNF | DNF | DNF | DNF | DNF | DNF |

Static Shear test at 100° F. with 1 Kg weight - Target exceed 720 minutes without failure (DNF = Did not fall with 24 hour period)
Comparison 1 - This is a commercially available fastening tape PSA (HL-1347) available from H.B. Product Comparison 1
Comparison 2 Rextac 2730 commercially available from Huntsman Corporation
Comparison 3 - This is a commercially available recrystallizing hot melt HL-1696 available from H.B. Fuller Co. as described in U.S. Pat. Nos. 5,627,229 and 5,624,986.
Comparison 1 and 2 failed to preform as desired and comparison 3 obtained adequate performance only at high add on amounts (greater than 4 mil).

Tab Attachment Adhesive Test

Samples are prepared follows. Adhesives were slot die coated onto silicone release liner and mated to a bi-laminated spun bond/thermal bond non-woven diaper tab material from BBA Non-wovens (BD-03-02) at 300° F. The adhesive was coated at a width of 20 mm wide and mated to one edge of the 4 inch wide BBA non-woven fabric. This laminate was then cut to a width of 38 mm to form a 38 mm by 4 inch diaper tab. The release liner was then removed and the adhesive pressed onto a baby diaper backsheet and then passed through a nip roll set at 30 psi. The time between coating the adhesives onto the BBA non-woven and forming the bond to the baby diaper backsheet was between one and two minutes. These constructs were then hung in a forced air oven set at 100° F. with 1-Kg weights attached to one end. Six replicates were tested for each adhesive at three different coat weights. The adhesive is considered to have passed the test if the average time to failure is greater than 720 minutes.

Viscosity is measured with test procedure ASTM D-2669, needle penetration is measured with test procedure ASTM D-1321, softening point is measured with test procedure ASTM D-6090, $T_g$ is measured with test procedure ASTM E-1640. Open time relates to the time the materials remain tacky after melt application as defined by a test method that is intended to provide information on the adhesive open time. In conducting the test, a Kraft/Kraft Laminate is made and the adhesive open time measured. The open time is defined as the elapsed time between adhesive application to the Kraft substrate and production of fiber tearing bonds between layers. Results are reported in seconds (maximum time) required to obtain at least 90% fiber surface of paper tear.

In the procedure, first place about 20 grams of sample, cut to about 1 mm size pieces, in an aluminum-weighing dish containing about 0.06 grams of a Isonox 129 antioxidant (stabilizer) or equivalent. Add a second equal portion of the antioxidant onto the top of the sample. Please the sample and dish in the oven set at 375±5° F. (190° C.) for 20±5 minutes.

Place the draw down bar or Bird applicator (or other suitable draw down bar with a 5 mil gap) in the oven at the same time, so that it will be at substantially the same temperature as the melt sample.

While the sample is conditioning, prepare the Kraft paper for running the open time by cutting a piece of the Kraft Paper at least 11" in length. Secure the Kraft paper to the draw down plate taped around the edges with the rough side up (this is the inside of the roll) ensuring that the paper is smooth and wrinkle free. Position a double thick paper towel at the bottom edge of the plate.

Cut seven Kraft strips approximately 8 inches in length and 1" wide. It is important that the width is not over 1" so that the rubber roller, which is 1¾" wide, can overlap the Kraft strips when rolling the strips in place. Mark the strip rough side with a pencil to identify the rough side.

At the end of the 15-minute conditioning period, using tongs and protective thermal gloves, remove the aluminum dish and Bird applicator from the oven. Place them on the hot plate next to the Kraft paper layout. Using a thermometer, slowly stir the sample in the dish. Continue stirring until the sample temperature reaches 375±5° F. Remove the applicator from the hot plate and position it at the top of the draw down plate. The long, beveled, bottom side of the applicator must be facing you.

Pour about 5 to 7 grams of the adhesive near the edge of the applicator. This will be about 3 cm in diameter. Start the draw down with the applicator; starting at the top, uniformly draw down the applicator with a constant even pressure. Avoid stopping at the middle of the paper. Continue the draw down until you have reached the bottom edge of the paper. Set the applicator aside.

The complete draw down will take about 1 second. Do not apply any downward pressure on the applicator when drawing it to you, as the applicator can tear the paper. At the end of the draw down, start the stop watch.

At 10, 20, 30, 40, and 60-second intervals, sequentially position one of the precut Kraft Strips (rough side down) across the applied coating. Immediately after positioning the strip, cover Kraft strip with a strip of the coated paper (slick side down), roll the strip three (3) times using the rubber roller. Across and back with the rubber roller is considered one roll. Do not apply any downward pressure on the rubber roller, the test is designed using the built in weight of the rubber roller.

After the last strip has been positioned and rolled, set the timer for 5 minutes. At the end of the 5 minute±5 second waiting period and starting with the first (10 sec.) strip, grasp the left end of the strip and with a left to right motion, peel back the paper strip at a 180° angle. Using a uniform motion, 1 to 1½ seconds, peel the strip. If the strip breaks before completing the peel across the adhesive, then grasp the right end of the strip and in a reverse manner, peel from right to left. In sequential order, peel the remaining strips. Open time is the maximum time taken to provide at least 90% fiber or paper tear, i.e. paper fibers can be seen across 90% of the area covered by the tear off strip. Report open time in seconds.

The adhesive can comprise, in its entirety, one of a number of useful polymers, a blend of polymers, or alternatively the adhesive can comprise a hot melt adhesive comprising at least one polymer admixed with other thermoplastic diluents such as tackifying resins, etc. The polymer provides the important adhesive properties such as open time, shear strength, tensile strength, cohesiveness and viscosity. The polymer is typically combined with a tackifier or other material to modify the adhesive properties as little as possible for use in the intended application. The blend of materials is formulated to exhibit the same desired properties. Typical additives include tackifying resins plasticizing agents and oils and extenders such as organic or inorganic fillers and extenders. The composition of the present invention is preferably made by first preparing the thermoplastic component by melting and blending all the thermoplastic ingredients. The thermoplastic composition with or without additives can be pelletized, pillowed, or cast into molds or drums, etc., for subsequent remelting and application. Alternatively, all the ingredients may be fed simultaneously at the appropriate rates into an extruder if desired for compounding.

The above specification, examples and data provide a complete description of the manufacture and use of the composition of the invention. Since many embodiments of the invention can be made without departing from the spirit and scope of the invention, the invention resides in the claims hereinafter appended.

I claim:

1. A disposable diaper or an adult incontinent diaper comprising a non-woven layer, an absorbent layer and a film cover, the diaper further comprising a set of tabs, each tab comprising cooperating fastening means, the tabs attached to the disposable garment using an adhesive consisting of an amorphous alpha olefin polymer comprising greater than 50 wt.% of a 1-butene monomer, the polymer having a tensile strength of about 300 to 4000 kPa and an adhesive open time of at least 200 seconds.

2. The article of claim 1 wherein the polymer has greater than 60 wt.% 1-butene monomer and a needle penetration of 0.5 to 2 mm, a Ring and Ball softening point less than about 100° C., a glass transition temperature less than about −20° C. and a Brookfield viscosity of greater than 2500 cP at 190° C.

3. The article of claim 1 wherein the polymer comprises 60 to 70 wt.% 1-butene and 30-40% propylene and less than 10% crystallinity.

4. The article of claim 2 wherein the polymer also comprises 1-10 wt.% of an additional olefin monomer.

5. The article of claim 1 wherein the polymer has greater than 60 wt.% 1-butene monomer and the adhesive comprises a thickness of about 0.05 to 0.2 mm.

6. The article of claim 1 wherein the polymer has greater than 75 wt.% 1-butene monomer and the adhesive comprises a thickness of about 0.02 to 0.1 mm.

7. The article of claim 1 wherein the tab comprises a polymer film having a thickness of about 0.1 to 0.5 mm a width of 1 to 5 cm and a length of 5 to 15 cm.

8. The article of claim 1 wherein the open time of the adhesive is greater than 400 seconds.

9. The article of claim 1 wherein the viscosity is greater than about 2700 cP.

10. The article of claim 1 wherein the fastening means comprises a hook and loop system.

11. The method of manufacturing a disposable diaper, or an adult incontinent diaper, the method comprising the steps of forming, between a film layer and a tab fastener in a diaper comprising a non-woven layer and an absorbent layer, an attachment layer comprising an adhesive consisting of an amorphous alpha olefin polymer comprising-greater than 50 wt.% of a 1-butene monomer, the polymer having a tensile strength of about 300 to 4000 kPa and an adhesive open time of at least 200 seconds.

12. The method of claim 11 wherein the polymer has a needle penetration of 0.5 to 2 mm, a Ring and Ball softening point less than about 100° C., a glass transition temperature less than about 30° C. and a Brookfield viscosity of greater than 2700 cP at 190° C.

13. The method of claim 11 wherein the polymer comprises 60 to 70 wt.% 1-butene and 30-40% propylene and less than 10% crystallinity.

14. The method of claim 13 wherein the polymer also comprises 1-10 wt.% of an additional olefin monomer.

15. The method of claim 11 wherein the polymer has greater than 60 wt.% 1-butene monomer and the adhesive comprises a thickness of about 0.02 to 0.22 mm.

16. The method of claim 11 wherein the polymer has greater than 75 wt.% 1-butene monomer and the adhesive comprises a thickness of about 0.05 to 0.1 mm.

17. The method of clam 11 wherein the tab comprises a polymer film having a thickness of about 0.1 to 0.5 mm a width of 1 to 5 cm and a length of 5 to 15 cm.

18. The method of claim 11 wherein the open time of the adhesive is greater than 400 seconds.

19. The method of claim 11 wherein the viscosity is greater than about 2700 cP.

20. The method of claim 11 wherein the fastening means comprises a hook and loop system.

21. The method of claim 11 wherein the attachment layer is formed at room temperature.

22. A tab for a disposable diaper and an adhesive layer for the tab comprising a flexible film, positioning fastening means and an attachment adhesive, adhering the tab to the diaper, the adhesive consisting of an amorphous alpha olefin polymer comprising-greater than 50 wt.% of a 1-butene monomer, the polymer having a tensile strength of about 300 to 4000 kPa and an adhesive open time of at least 200 seconds.

23. The tab of claim 22 wherein the polymer has a needle penetration of 0.5 to 2 mm, a Ring and Ball softening point less than about 100° C., a glass transition temperature less than about 30° C. and a Brookfield viscosity of greater than 2700 cP at 190° C.

24. The tab of claim 22 wherein the polymer comprises 60 to 70 wt.% 1-butene and 30-40% propylene and less than 10% crystallinity.

25. The tab of claim 24 wherein the polymer also comprises 1-10 wt.% of an additional olefin monomer.

26. The tab of claim 22 wherein the polymer has greater than 60 wt.% 1- butene monomer and the adhesive comprises a thickness of about 0.02 to 0.2 mm at an amount of 1 to 10 gm-m$^{-2}$.

27. The tab of claim 22 wherein the polymer has greater than 75 wt.% 1- butene monomer and the adhesive comprises a thickness of about 0.05 to 0.1 mm at an amount of 1 to 10 gm-m$^{-2}$.

28. The tab of clam 22 wherein the tab comprises a polymer film having a thickness of about 0.1 to 0.5 mm a width of 1 to 5 cm and a length of 5 to 15 cm.

29. The tab of claim 22 wherein the open time of the adhesive is greater than 400 seconds.

30. The tab of claim 22 wherein the viscosity is greater than about 2700 cP.

31. The tab of claim 22 wherein the fastening means comprises a hook and loop system.

32. A disposable diaper or an adult incontinent diaper comprising a non-woven layer, an absorbent layer and a film cover, the diaper further comprising a set of tabs, each tab comprising cooperating fastening means, the tabs attached to the disposable garment using an adhesive comprising an amorphous alpha olefin polymer and a diluent additive, the polymer comprising greater than 50 wt.% of a 1-butene monomer, the polymer having a tensile strength of about 300 to 4000 kPa and an adhesive open time of at least 200 seconds.

33. The article of claim 32 wherein the polymer has greater than 60 wt.% 1-butene monomer and a needle penetration of 0.5 to 2 mm, a Ring and Ball softening point less than about 100° C., a glass transition temperature less than about −20° C. and a Brookfield viscosity of greater than 2500 cP at 190° C.

34. The article of claim 32 wherein the polymer comprises 60 to 70 wt.% 1-butene and 30-40% propylene and less than 10% crystallinity.

35. The article of claim 33 wherein the diluent additive comprises a tackifing agent, a plasticizing agent an extender agent or mixtures thereof.

36. The article of claim 32 wherein the polymer has greater than 60 wt.% 1-butene monomer and the adhesive comprises a thickness of about 0.05 to 0.2 mm at an add on amount of 1 to 10 gm-m$^{-2}$.

37. The article of claim 32 wherein the polymer has greater than 75 wt.% 1-butene monomer and the adhesive comprises a thickness of about 0.02 to 0.1 mm at an add on amount of 1 to 10 gm-m$^{-2}$.

38. The article of clam 32 wherein the tab comprises a polymer film having a thickness of about 0.1 to 0.5 mm a width of 1 to 5 cm and a length of 5 to 15 cm.

39. The article of claim 32 wherein the open time of the adhesive is greater than 400 seconds.

40. The article of claim 32 wherein the viscosity is greater than about 2700 cP.

41. The article of claim 32 wherein the fastening means comprises a hook and loop system.

42. A method of manufacturing a disposable diaper, or an adult incontinent diaper, the method comprising the steps of forming, between a film layer and a tab fastener in a garment comprising a non-woven layer and an absorbent layer, an attachment layer comprising an adhesive comprising an amorphous alpha olefin polymer and a diluent additive comprising-greater than 50 wt.% of a 1-butene monomer, the polymer having a tensile strength of about 300 to 4000 kPa and an adhesive open time of at least 200 seconds.

43. The method of claim 12 wherein the polymer has a needle penetration of 0.5 to 2 mm, a Ring and Ball softening point less than about 100° C., a glass transition temperature less than about 30° C. and a Brookfield viscosity of greater than 2700 cP at 190° C.

44. The method of claim 42 wherein the polymer comprises 60 to 70 wt.% 1-butene and 30-40% propylene and less than 10% crystallinity.

45. The method of claim 44 wherein the diluent additive comprises a tachfying agent or platicizing agent, an extender agent or mixtures thereof.

46. The method of claim 42 wherein the polymer has greater than 60 wt.% 1-butene monomer and the adhesive comprises a thickness of about 0.02 to 0.22 mm at an amount of 1 to 10 gm-m$^{-2}$.

47. The method of claim 42 wherein the polymer has greater than 75 wt.% 1-butene monomer and the adhesive comprises a thickness of about 0.05 to 0.1 mm at an on amount of 1 to 10 gm-m$^{-2}$.

48. The method of claim 42 wherein the polymer comprises 60 to 70 wt.% 1-butene and 30-40% propylene and less than 10% crystallinity.

49. The method of claim 44 wherein the polymer also comprises 1-10 wt.% of an additional olefin monomer.

50. The method of claim 42 wherein the polymer has greater than 60 wt.% 1- butene monomer and the adhesive comprises a thickness of about 0.02 to 0.22 mm.

51. The method of claim 42 wherein the polymer has greater than 75 wt.% 1- butene monomer and the adhesive comprises a thickness of about 0.05 to 0.1 mm.

52. method of clam 42 wherein the tab comprises a polymer film having a thickness of about 0.1 to 0.5 mm a width of 1 to 5 cm and a length of 5 to 15 cm.

53. The method of claim 42 wherein the open time of the adhesive is greater than 400 seconds.

54. The method of claim 42 wherein the viscosity is greater than about 2700 cP.

55. The method of claim 42 wherein the fastening means comprises a hook and loop system.

56. The method of claim 42 wherein the attachment layer is formed at room temperature.

57. A tab for a disposable-diaper, the tab comprising a flexible film, positioning fastening means and an attachment adhesive, adhering the tab to the disposable garment, the adhesive comprising an amorphous alpha olefin polymer and a diluent additive, the polymer comprising-greater than 50 wt.% of a 1-butene monomer, the polymer having a tensile strength of about 300 to 4000 kPa and an adhesive open time of at least 200 seconds.

58. The tab of claim 57 wherein the polymer has a needle penetration of 0.5 to 2 mm, a Ring and Ball softening point less than about 100° C., a glass transition temperature less than about 30° C. and a Brookfield viscosity of greater than 2700 cP at 190° C.

59. The tab of claim 57 wherein the polymer comprises 60 to 70 wt.% 1-butene and 30-40% propylene and less than 10% crystallinity.

60. The tab of claim 59 wherein the polymer also comprises 1-10 wt.% of an additional olefin monomer.

61. The tab of claim 57 wherein the polymer has greater than 60 wt.% 1- butene monomer and the adhesive comprises a thickness of about 0.02 to 0.2 mm at an amount of 1 to 10 gm-m $^{-2}$.

62. The tab of claim 57 wherein the polymer has greater than 75 wt.% 1- butene monomer and the adhesive comprises a thickness of about 0.05 to 0.1 mm at an amount of 1 to 10 gm-m $^{-2}$.

63. The tab of clam 57 wherein the tab comprises a polymer film having a thickness of about 0.1 to 0.5 mm a width of 1 to 5 cm and a length of 5 to 15 cm.

64. The tab of claim 57 wherein the open time of the adhesive is greater than 400 seconds.

65. The tab of claim 57 wherein the viscosity is greater than about 2700 cP.

66. The tab of claim 57 wherein the fastening means comprises a hook and loop system.

\* \* \* \* \*

UNITED STATES PATENT AND TRADEMARK OFFICE
CERTIFICATE OF CORRECTION

PATENT NO.        : 8,048,054 B2                                      Page 1 of 1
APPLICATION NO.   : 11/582842
DATED             : November 1, 2011
INVENTOR(S)       : William L. Bunnelle It is certified that error appears in the above-identified patent and that said Letters Patent is hereby corrected as shown below:

In column 13, line 5, claim 35, after "agent" please insert --,--

In column 13, line 51, claim 47, after "an" please insert --add--

In column 14, line 8, claim 52, before "method" please insert --The--

In column 14, line 8, claim 52, please delete "clam" and insert --claim--

Signed and Sealed this
Fifteenth Day of May, 2012

David J. Kappos
*Director of the United States Patent and Trademark Office*